(12) United States Patent
Boomgaarden

(10) Patent No.: US 7,090,396 B2
(45) Date of Patent: Aug. 15, 2006

(54) SYSTEMS, METHODS AND APPARATUS OF A RADIOGRAPHIC POSITIONER

(75) Inventor: Jonathon Carl Boomgaarden, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 53 days.

(21) Appl. No.: 10/966,504

(22) Filed: Oct. 15, 2004

(65) Prior Publication Data

US 2006/0083353 A1 Apr. 20, 2006

(51) Int. Cl.
*H05G 1/02* (2006.01)
(52) U.S. Cl. ........................... 378/196; 378/197
(58) Field of Classification Search ............... 378/193, 378/195, 196, 197
See application file for complete search history.

(56) References Cited

U.S. PATENT DOCUMENTS

| | | | | |
|---|---|---|---|---|
| 5,636,259 A | * | 6/1997 | Khutoryansky et al. | .... 378/197 |
| 5,751,788 A | * | 5/1998 | Khutoryansky et al. | .... 378/197 |
| 5,768,336 A | * | 6/1998 | Khutoryansky et al. | .... 378/116 |
| 5,870,450 A | * | 2/1999 | Khutoryansky et al. | .... 378/197 |
| 5,917,882 A | * | 6/1999 | Khutoryansky et al. | .... 378/116 |
| 6,128,006 A | | 10/2000 | Rosenberg et al. | ......... 345/163 |
| 6,459,226 B1 | | 10/2002 | Zettel et al. | ............... 318/560 |

* cited by examiner

*Primary Examiner*—Courtney Thomas

(74) *Attorney, Agent, or Firm*—Carl B. Horton; Peter J. Vogel; Michael G. Smith

(57) ABSTRACT

Systems, methods and apparatus are provided through which, in one embodiment, an X-ray source and collimator are positioned relative to an image receptor for imaging of a subject.

39 Claims, 11 Drawing Sheets

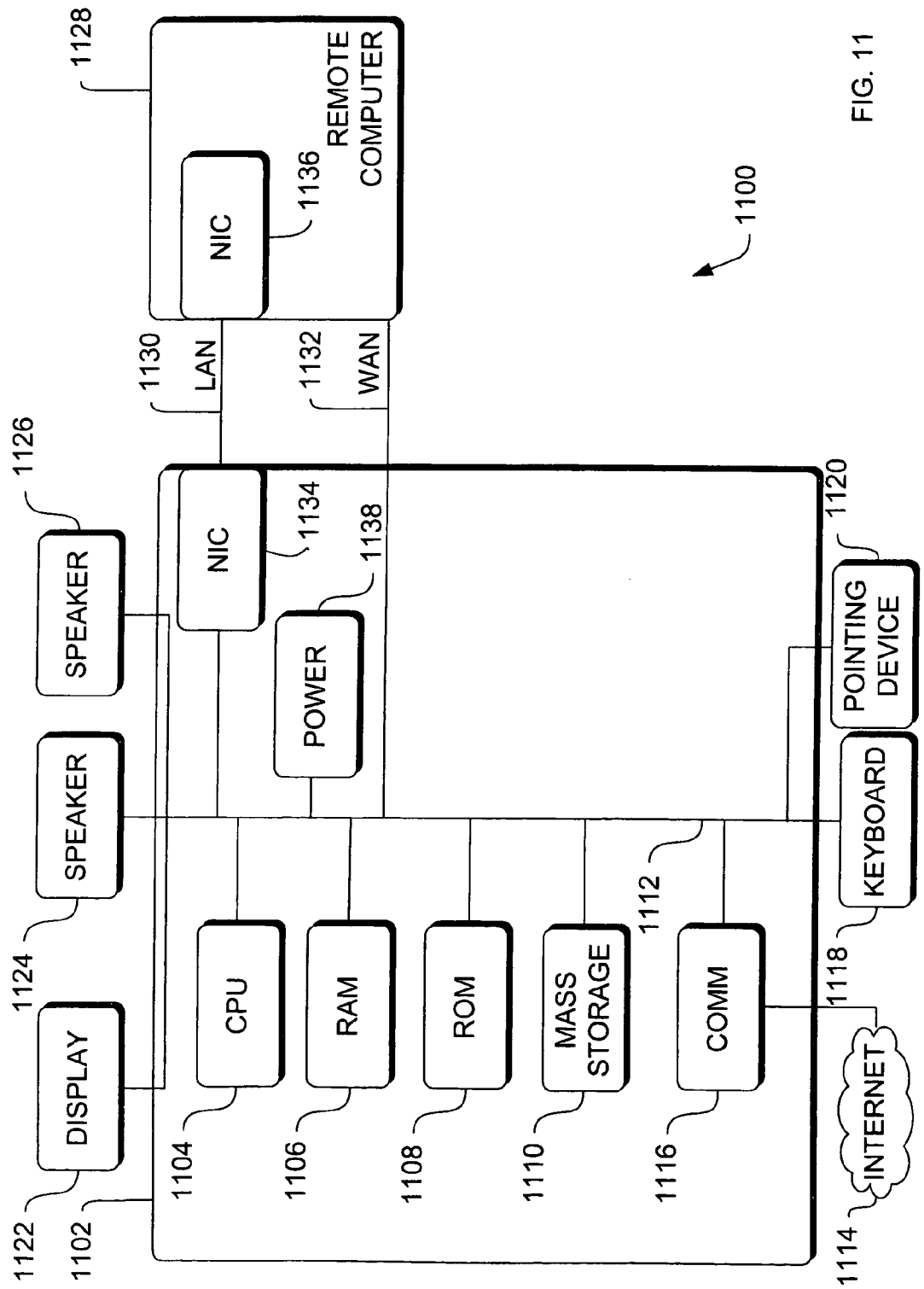

SYSTEMS, METHODS AND APPARATUS OF A RADIOGRAPHIC POSITIONER

RELATED APPLICATION

This application is related to U.S. Pat. No. 6,459,226 issued Oct. 1, 2002 entitled "Method and Apparatus for Accurate Powered Deceleration and Immobilization of Manually Operated Mechanism."

FIELD OF THE INVENTION

This invention relates generally to positioning apparatus, and more particularly to control logic to operate the positioning apparatus.

BACKGROUND OF THE INVENTION

Conventional radiographic examination rooms include a radiographic table and/or radiographic wallstand. The radiographic table and/or radiographic wallstand each contain an image receptor. Medical imaging equipment such as an X-ray source and the collimator is mounted to an overhead tube support (OTS) in the vicinity of the radiographic table and/or the radiographic wallstand for performing diagnostic imaging procedures. The X-ray source and the collimator comprise a tube mount assembly.

The tube mount assembly is aligned with the receptor for imaging of a subject. To align the tube mount assembly with a receptor, the tube mount assembly and OTS move in three linear motions (lateral, longitudinal, vertical) which are perpendicular to each other, and the tube mount assembly moves in two rotational rotations (rotation about the vertical axis, and rotation about one horizontal axis), for a total of five axes.

Manual positioning of the X-ray source, collimator and OTS is performed by an operator releasing locks on each of the five axes, moving the tube mount assembly to a position of alignment with a receptor, the position being indicated by a "detent," and stopping the tube mount assembly at that position for each of the five axes. The detent is a means of indicating to the operator that the OTS has reached an aligned position along an axis, either by mechanical sensation, of a wheel dropping into a groove, or of an electromechanical lock engaging, or of a visual indication.

Because alignment of the tube mount assembly with a receptor has been mandated by US Federal law, (DHHS CFR21 Subchapter J), many different techniques have been developed to determine proper alignment, and to secure the tube mount assembly in a properly aligned position. In some techniques the operator presses a manual release for a tooth-and-slot lock, and moves the axis until the tube mount assembly reaches the proper position at which the tooth is engaged in another slot. In other implementations, the operator presses a button, which releases an electromechanical friction lock, and when the proper position is reached, the electromechanical friction lock is again engaged. In some other implementations, the "detent" is created by a roller on a smooth surface engaging a transverse slot, creating a tactile perception to the operator that the proper position has been reached.

What is common to all of these techniques is that at least one detent is at a fixed position along an axis of motion at a position in which the tube mount assembly is aligned with a receptor. The operator seeks a detent position by releasing some holding means, or overcoming friction, in order to move the tube mount assembly along that axis to the detent position. When the detent position is reached an indicator will indicate that the detent position has been reached. The indication is a tactile sensation, an audible tone, and/or a visual indication such as a light, etc. Once the operator releases control of that axis of motion, further motion past the detent position is prevented, either by friction, by spring pressure on a wheel in a slot, and/or by engagement of a tooth in a slot, or by some other means. While detent positions may be different for a radiographic table receptor than for a radiographic wallstand image receptor, for each receptor, they are fixed positions of the axes.

One limitation of conventional systems is that the positions of the detents are relative to the axes of motion of the OTS. As a result of the relativity of the positions, it is necessary to align the receptors of the radiographic table and radiographic wallstand parallel or perpendicular to the linear axes of motion of the OTS. To understand this, consider the two examples below:

EXAMPLE A: In one example, there is a lateral detent for the table, which is a fixed position across the width of the table, which aligns with the center of the image receptor.

The image receptor is provided means to move along the length of the table, and (in one embodiment) has a motorized drive, which tracks the position of the X-ray tube and collimator attached to the OTS. So it is possible to position the OTS in the lateral detent, and manually move the OTS along the table, maintaining alignment with the receptor. This alignment is maintained because the lateral position of the OTS is locked at a specific location along the lateral positioning rails, and the longitudinal position of the receptor tracks the longitudinal position of the OTS as it moves along the longitudinal positioning rails.

The detent position is a fixed location of the OTS on the lateral positioning rails.

However, it can be clearly seen that the lateral detent achieved by this means is only as accurate as the alignment of the longitudinal direction of the table with the longitudinal direction of motion of the OTS in the longitudinal positioning rails.

An additional detent position is provided by a fixed mechanical stop to maintain the rotational position of the OTS about the vertical rotational axis, so that the rotational position of the X-ray field about the center of the image field is correct.

An additional detent is provided to maintain the proper vertical separation between the X-ray tube focal spot and the receptor.

An additional detent may be provided for the rotational position of the horizontal rotational axis, (either a hard stop, or a user perceptible position) and/or the longitudinal motion of the receptor may be adjusted to correctly position the receptor if the horizontal axis of the OTS is rotated.

This requires the alignment of the table to the positioning rails of the OTS, as stated earlier.

EXAMPLE B: In another example, a detent position provides alignment of the X-ray tube and the collimator to the horizontal center of the radiographic wallstand image receptor, when the radiographic wallstand receptor is in the vertical position.

When the OTS is moved manually nearer or farther away from the radiographic wallstand, it is required that the focal spot of the X-ray source assembly remain the centerline extending from the image receptor perpendicular to the image plane.

This is accomplished by placing the image plane perpendicular to either the lateral or longitudinal positioning rails.

The X-ray tube and collimator is placed in the proper position relative to the radiographic wallstand as follows:

The horizontal rotational axis is rotated so that the central ray of the X-ray field is in the horizontal plane. A detent is provided for this position.

The vertical rotation axis is rotated so that the central ray lies along either the lateral positioning rails, or the longitudinal positioning rails, whichever is perpendicular to the image plane. A detent or lock of some sort is provided for this position.

The OTS is moved along the lateral or longitudinal positioning rails (whichever is parallel to the image plane) until the central ray of the X-ray field is at the horizontal center of the image receptor. A detent is provided for this position, as a fixed position (within a tolerance) in the relevant horizontal motion axis.

The vertical extension of the OTS is adjusted so that the central ray of the X-ray field is at the vertical center of the image receptor. A detent is provided for this position, as a fixed position (within a tolerance) in the vertical motion axis.

The distance from the X-ray source to the image receptor may now be varied by moving along the remaining set of positioning rails, and the image will remain properly centered.

Note that the sequence above is arbitrary, and in fact other variations exist, such as automatic positioning of the OTS to match the vertical position of the radiographic wallstand image receptor. In addition, note that the receptor for the radiographic wallstand can be rotated over a range of angles, for example, from −20 to +90 degrees, relative to the vertical position.

However, in the two examples above, it can be seen that it is necessary for the table and radiographic wallstand to be aligned at zero or 90 degrees relative to the lateral and/or longitudinal positioning rails of the OTS, and the accuracy with which the manual motions described will "track" the image receptor is determined by the accuracy of this alignment. This limits the flexibility of room configurations, and at the same time, limits the accuracy of positioning.

Manual positioning in conventional systems requires releasing one or more locks for the axes of the OTS, typically using switches mounted on the user interface, or on the collimator, and pushing the tube mount assembly in the desired direction of motion. Motion is prevented in those directions for which the locks or detents are not released in this manner. It should be noted that the tube mount assembly may be locked in any position of the translation motions, and not only in the detent position.

Additionally, in conventional systems, the radiographic wallstand image receptor is typically mounted to the floor or wall, and the X-ray tube suspension is typically mounted to the ceiling. As a result of this, the motion of each is not necessarily perfectly vertical, as there may be some leaning of the radiographic wallstand, and the extending column of the OTS may not produce perfectly vertical motion. Additionally, both devices may bow or distort due to the influence of gravity, as they are not perfectly rigid.

As a consequence of bowing or distortion, the alignment of a focal spot of the X-ray tube is only accurately aligned for one particular height of the radiographic wallstand image receptor, and thus is likely to be misaligned at other heights.

Additionally, in conventional systems, the lock release switches on the UIF or the collimator control specific locks, and this causes some confusion for the operator, because if the X-ray tube and collimator are rotated 90 degrees about the vertical rotation axis of the OTS, the operator must remember that the function of the switches is now reversed, in that the motion of the OTS relative to the operator has not rotated. Also, at intermediate angles, the motion allowed is at skewed angles, relative to the operator. A more intuitive way of manually moving the OTS would improve usability of the tube mount assembly.

For the reasons stated above, and for other reasons stated below which will become apparent to those skilled in the art upon reading and understanding the present specification, there is a need in the art to increase the extent of flexibility of room configurations and improve the accuracy of positioning of the apparatus. There is also a need to maintain proper alignment over the full range of travel of the radiographic wallstand image receptor. There is a further need in the art for an ability to correct for imperfections in geometry in the apparatus and to allow for greater tolerance in precision in manufacturing and installation. This is an additional need in the art to reduce confusion of the operator in the relationship between the function of the switches and the motion of the OTS. There is also a need for a system that accommodates an image receptor of a wallstand or a table positioned at an angle other than 0 or 90 degrees to a positioning rails.

BRIEF DESCRIPTION OF THE INVENTION

The above-mentioned shortcomings, disadvantages and problems are addressed herein, which will be understood by reading and studying the following specification.

In one aspect, an apparatus to image a subject includes a radiographic positioning apparatus that further includes at least one motorized drive for each of five axes of motion of the radiographic positioning apparatus to provide motion along each of the axes, and the apparatus also includes a control unit operably coupled to each of the motorized drives.

In another aspect, the control unit includes a processor; and control logic operable on the processor to select a rotational detent to the extent that at least one of the axis is aligned to a radiographic image receptor, and to constrain movement of the at least one axis to the extent that manual positioning is along and across a plane parallel to the image receptor.

In yet another aspect, the five axes of motion of a longitudinal axis, a lateral axis, a vertical axis, a rotational vertical axis, and a rotational horizontal axis.

In still another aspect, the control logic to select a rotational detent further includes control logic to determine at least one detent position for the vertical rotation axis of a tube mount assembly from an angle at which the radiographic image receptor is positioned relative to a lateral positioning rail and a longitudinal positioning rail.

In a further aspect, the control logic to constraining further includes control logic to constrain movement of the tube mount assembly to the extent that manual positioning is not along a lateral positioning rail and a longitudinal positioning rail.

In yet a further aspect, the radiographic image receptor can be mounted to a radiographic table or a radiographic wallstand.

In still yet a further aspect, a method includes determining if a speed of movement of medical imaging equipment is commanded by a processor along a first axis of movement of the equipment at greater than a maximum speed; if so a clutch that connects the motorized drive to positioning rail in the first axis is released, which allows the equipment to move freely along that axis.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 11 is a block diagram of the hardware and operating environment in which different embodiments can be practiced.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, embodiments of methods are described. In the third section, apparatus of embodiments are described. In the fourth section, the hardware and the operating environment in conjunction with which embodiments may be practiced are described. Finally, in the fifth section, a conclusion of the detailed description is provided.

System Level Overview

Figure 1:
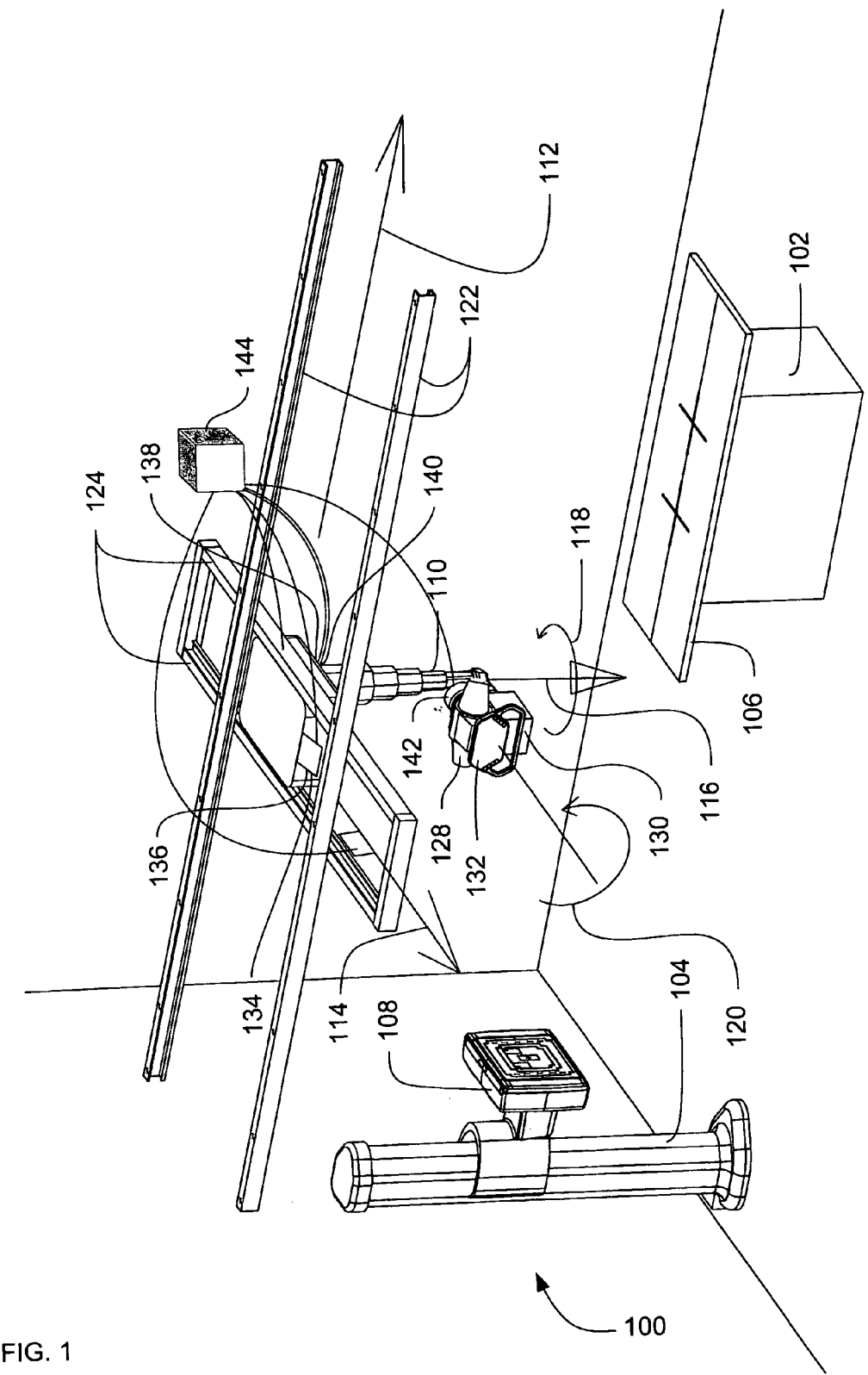
FIG. 1 is a diagram illustrating a system-level overview of an embodiment of a radiographic positioning system.

FIG. 1 is a diagram illustrating a system-level overview of an embodiment of a radiographic positioning system 100. System 100 improves the accuracy of positioning of the tube mount assembly, maintains proper alignment of the tube mount assembly with the radiographic image receptors over the full range of travel of the tube mount assembly, provides an ability to correct for imperfections in geometry in the tube mount assembly and to allow for greater tolerance in precision in manufacturing and installation, and reduces confusion of the operator in the relationship between the function of the switches and the motion of the overhead tube support (OTS).

System 100 includes a radiographic table 102 and/or a radiographic wallstand 104. The radiographic table 102 and the wallstand 104 each contain an image receptor, 106 and 108, respectively.

An overhead tube support (OTS) 110 for performing diagnostic imaging procedures is also included. The OTS 110 provides three linear motions (longitudinal X 112, lateral Y 114 and vertical Z 116) which are perpendicular to each other, and two rotational rotations (rotation about the vertical axis "a" 118, and rotation about one horizontal axis "b" 120).

Longitudinal positioning rails 122 are mounted to a ceiling (not shown). Lateral positioning rails 124 move along the longitudinal positioning rails 122 in the longitudinal X 112 motion. In other embodiments, the lateral positioning rails 124 are mounted to a ceiling and the longitudinal positioning rails 122 move along the lateral positioning rails 124 in the lateral Y 114 motion.

A carriage 126 moves along lateral positioning rails 124 in the lateral Y 114 motion. The OTS 110 is mounted on the carriage 126. A tube mount assembly 132 includes an X-ray source 128 and collimator 130. The tube mount assembly 132 is mounted to the OTS 110. The tube mount assembly 132 and/or the OTS 110 rotate about the vertical "a" 118 axis and the vertical "b" 120 axis.

The OTS 110 can be positioned at any attitude and position within the reaches of radiographic system 100. This flexibility in positioning is important in achieving alignment of the OTS 110 to an image receptor for imaging of a subject that is positioned on the radiographic table 102 or the radiographic wallstand 104. The alignment of the OTS 110 with an image receptor may be directed and/or controlled automatically by a control unit 144 or the alignment may be directed and/or controlled manually.

The lateral positioning rails 124 are operably coupled to the longitudinal positioning rails 122 through one or more first motorized drives 134. The carriage 126 is operably coupled to the lateral positioning rails 124 through one or more second motorized drives 136. In some embodiments, the OTS 110 is operably coupled to the carriage 126 through one or more third motorized drives 138 that rotates the OTS about the vertical Z 116. In some embodiments, the OTS 110 is also operably coupled to the carriage 126 through one or more fourth motorized drives 140 that extends the OTS along the vertical Z 116. In some embodiments, the X-ray source 128 is operably coupled to the OTS 110 through one or more fifth motorized drives 142 that rotate the X-ray source 128 about the horizontal axis "b" 120.

Each motorized drive includes a motor, and a position feedback measuring device, and in some embodiments a clutch and/or a lock or a brake. Each position feedback measuring device further includes a potentiometer, an encoder, a resolver, or a similar device. In the embodiments that lack a clutch, an efficient motor (having high quality bearings and high quality gears) is directly coupled, so that in manual motion the operator cause rotation of the motor armature as well as the OTS.

A control unit 144 is operably coupled to the one or more first motorized drives 134, the one or more second motorized drives 136, the one or more third motorized drives 138, the one or more fourth motorized drives 140 and the one or more fifth motorized drives 142. The control unit 144 controls operation of the motorized drives, which positions the X-ray source 128 and collimator 130 into alignment with a radiographic receptor 106 or 108.

In some implementations, more than one control unit 144 is included in system 100. Each control unit controls one or more motorized drives 134, 136, 138, 140 and/or 142. For example, in one implementation system 100 includes one control unit for each motorized drive. Each control unit communicates with the other control units, directly, or through other computers. Each control unit includes a processor, such as processor 1104 in FIG. 11.

The control unit 144 improves the accuracy of positioning of the apparatus 128 and 130. The control unit 144 also maintains proper alignment of the apparatus 128 and 130 with the radiographic image receptors 106 and 108 over the full range of travel of the apparatus 128 and 130. The control unit 144 also provides an ability to correct for imperfections in geometry in the apparatus and to allow for greater tolerance in precision in manufacturing and installation. The control unit 144 also reduces confusion of the operator in the relationship between the function of the switches and the motion of the OTS because the positioning of the apparatus 128 and 130 is performed by the control unit 144.

The system level overview of the operation of an embodiment has been described in this section of the detailed description. A control unit 144 controls the motorized drives to position the X-ray source 128 and collimator 130 into alignment with a radiographic receptor 106 or 108.

While the system 100 is not limited to any particular radiographic table 102, radiographic wallstand 104, image receptors 106 and 108, OTS 110, longitudinal positioning rails 122, lateral positioning rails 124, a carriage 126, X-ray source 128, collimator 130 and control unit 144. For sake of clarity, a simplified radiographic table 102, radiographic wallstand 104, image receptors 106 and 108, OTS 110, longitudinal positioning rails 122, lateral positioning rails 124, a carriage 126, X-ray source 128, collimator 130, and control unit 144 have been described.

Methods of an Embodiment

In the previous section, an overview of the operation of an embodiment was described. In this section, the particular methods performed by a human of such an embodiment are described by reference to a series of flowcharts.

Figure 2:
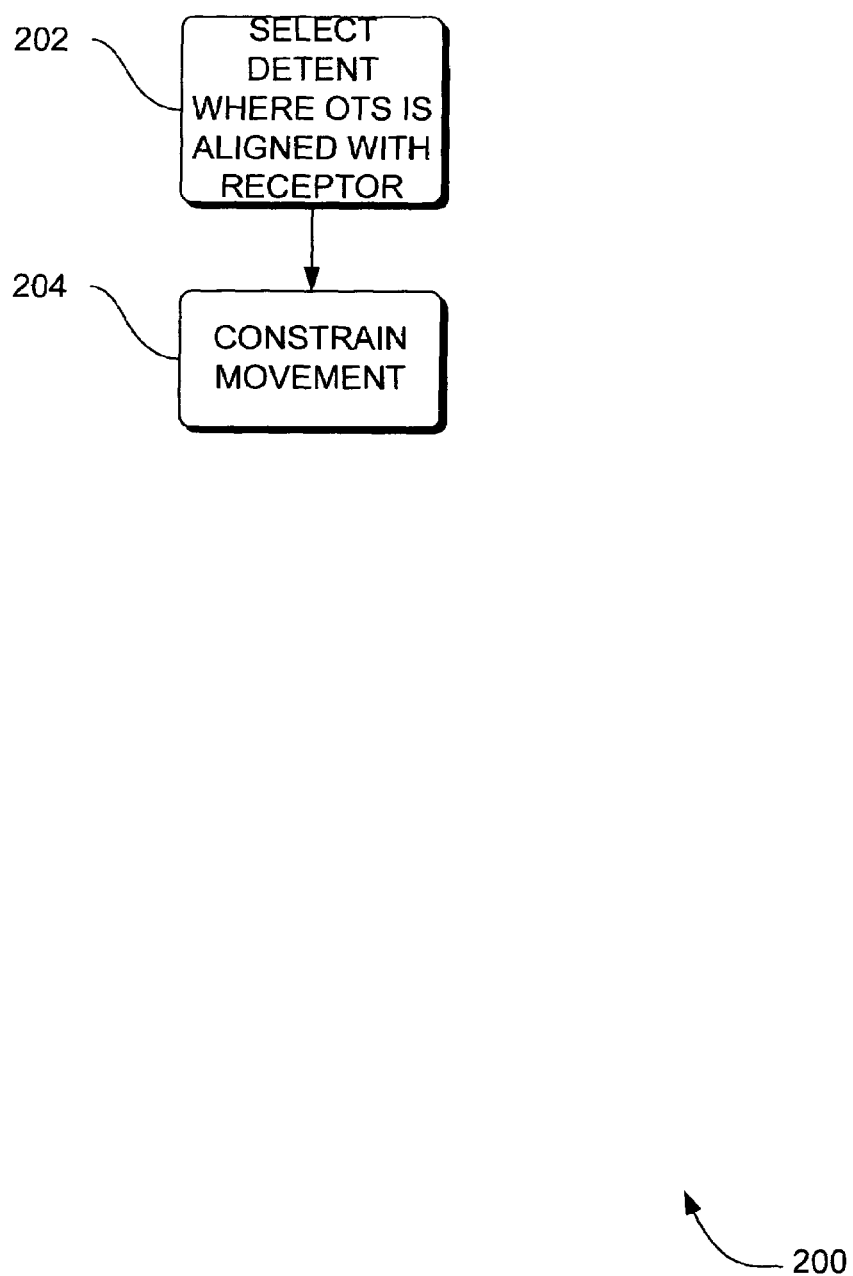
FIG. 2 is a flowchart of a method to manually position an overhead tube support so that proper alignment is maintained to a radiographic image receptor.

FIG. 2 is a flowchart of a method 200 to manually position an overhead tube support. The OTS is positioned so that proper alignment is achieved and/or maintained to a radiographic image receptor without regard to an angle about a vertical rotation axis at which the radiographic image receptor and the OTS motion axes are positioned relative to each other, according to an embodiment.

Method 200 includes selecting 202 a detent on a vertical rotation axis 118 or 120 where the tube mount assembly 132 is aligned to radiographic image receptor (table 106 or wallstand 108). A detent is provided for the rotational position of mount assembly 132 about the vertical axis 118, with the position of the detent being determined for each receptor (table 106 or wallstand 108) by the angle that the receptor makes to the longitudinal positioning rails 122 and the lateral positioning rails 124 of the OTS 110. One embodiment of action 202 is shown in FIG. 3.

Method 200 further includes constraining 204 movement of the tube mount assembly 132 to the extent that manual positioning is along and across the plane of the image receptor 106 and 108. One embodiment of action 204 is shown in FIG. 4.

Figure 3:
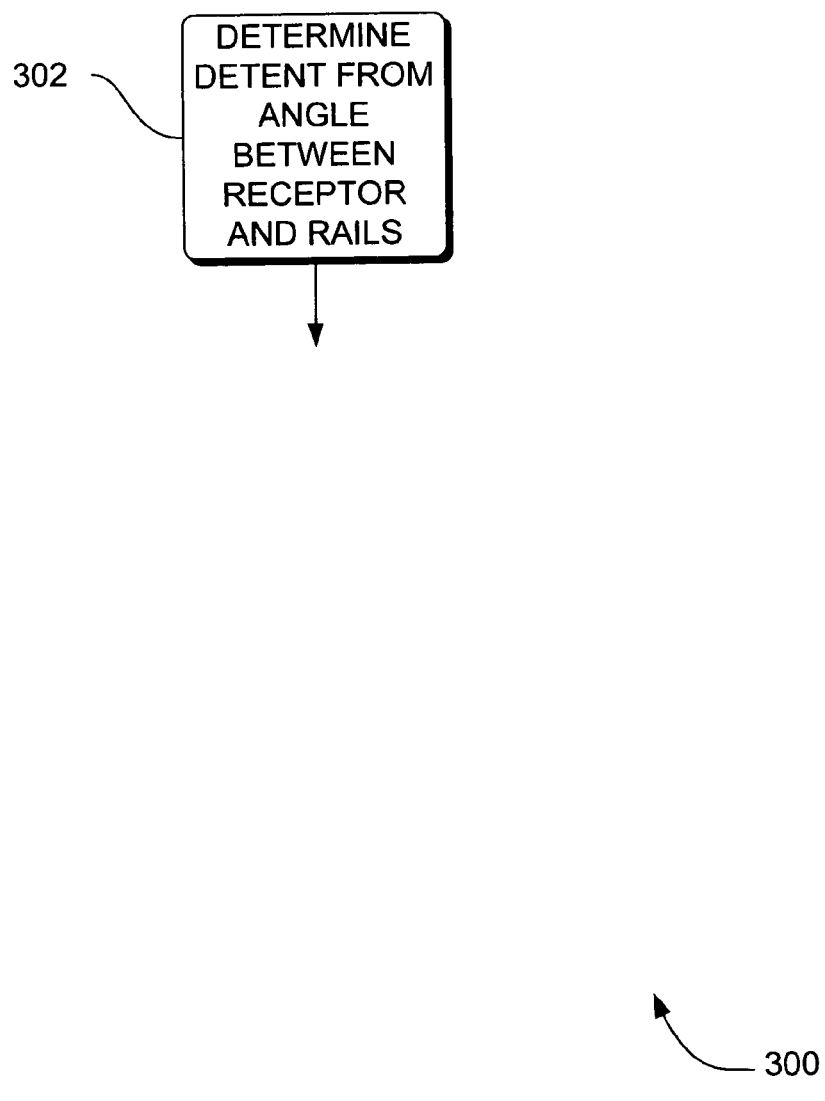
FIG. 3 is a flowchart of a method of selecting a rotational detent position.

FIG. 3 is a flowchart of a method 300 of selecting a rotational detent position. Method 300 is one embodiment of selecting 202 a rotational detent position. Method 300 includes determining or identifying 302 or at least one detent position for the vertical rotation axis 118 of the overhead tube support 110. The detent is determined 302 from an angle at which the radiographic image receptor 106 or 108 is installed or positioned relative to a lateral positioning rail 124 and a longitudinal positioning rail 122. The radiographic image receptor is mounted to either a radiographic table 102 or mounted to a radiographic wallstand 104.

Figure 4:
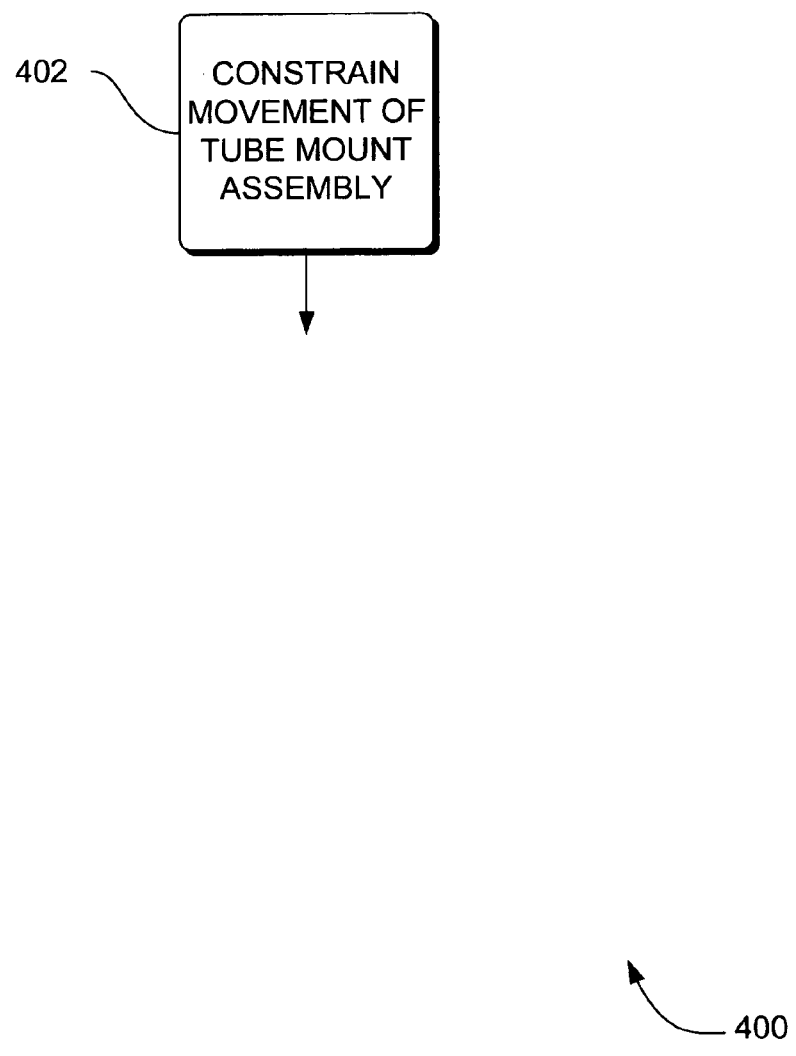
FIG. 4 is a flowchart of a method of constraining movement of a tube mount assembly.

FIG. 4 is a flowchart of a method 400 of constraining movement of a tube mount assembly 132. Method 400 is one embodiment of constraining 204 movement of the tube mount assembly 132 in FIG. 2. Method 400 includes constraining 402 movement of the tube mount assembly 132 to the extent that manual positioning is not performed along or relative to a lateral positioning rail 124 and a longitudinal positioning rail 122.

Figure 5:
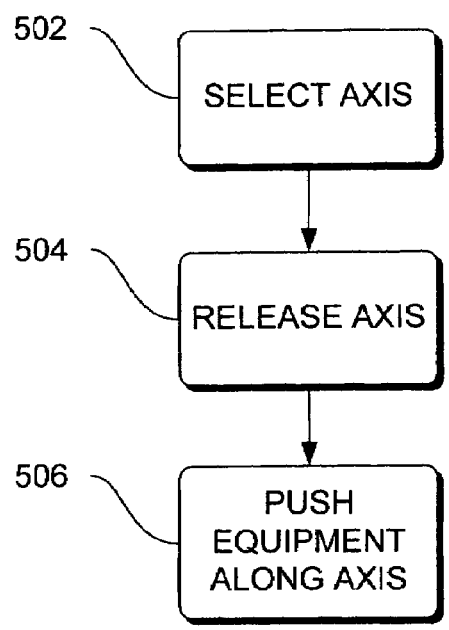
FIG. 5 is a flowchart of a method of positioning radiographic equipment preformed by a human, according to an embodiment.
Figure 5:
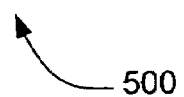
Figure 6:
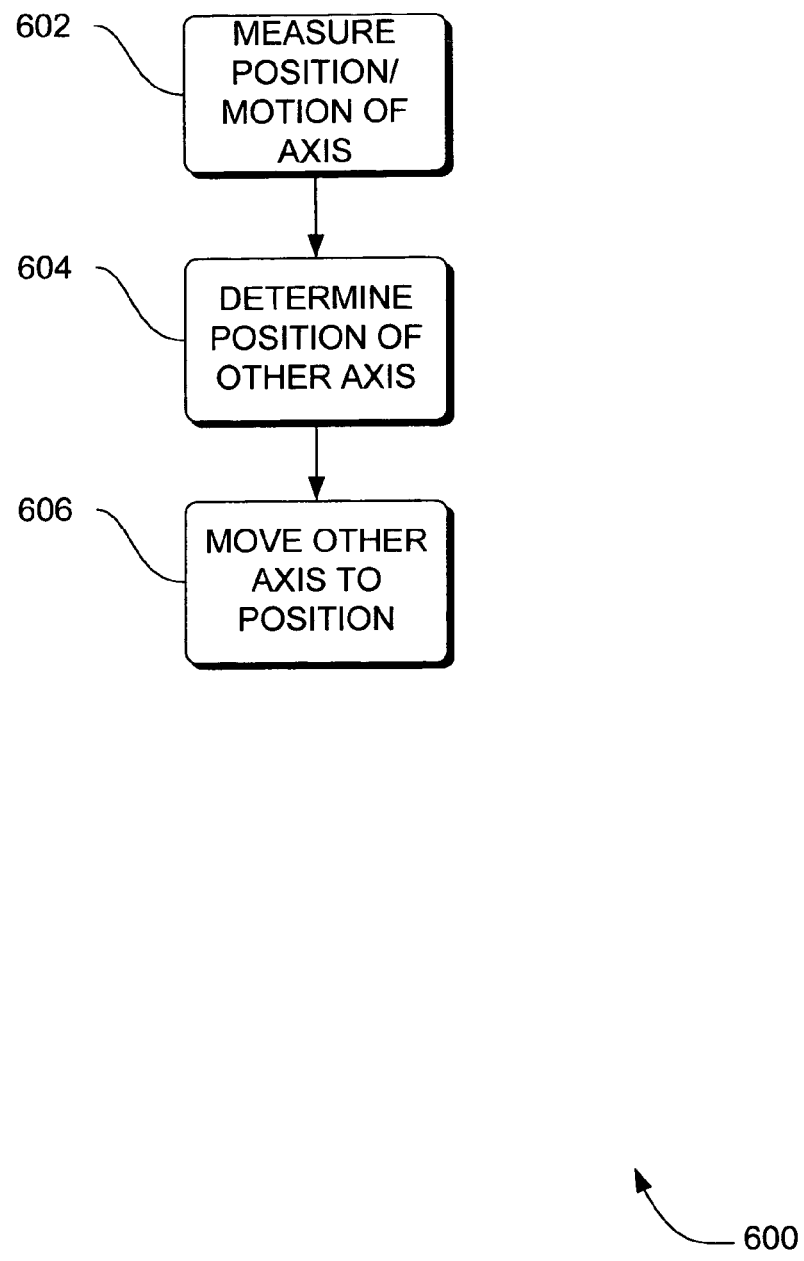
FIG. 6 is a flowchart of a method of positioning radiographic equipment performed by a processor, according to an embodiment.

Method 500 in FIG. 5 and method 600 in FIG. 6 are methods that are performed in conjunction with each other. Method 500 is performed by a human and method 600 is performed by a system or apparatus, such as system 100. In essence, methods 500 and 600 provide for a process that allows an operator of the system to move equipment manually along one axis wherein the system moves the equipment along another axis so that the equipment follows a straight line between the axes.

FIG. 5 is a flowchart of a method 500 of positioning radiographic equipment according to an embodiment performed by a human. Method 500 includes selecting 502 one axis of the tube mount assembly (132 in FIG. 1) to release. The selection is made from the angle of rotation of the tube mount assembly 132. In some embodiments of selecting 502, the axis of the tube mount assembly 132 that has a larger linear movement for motion in the direction of motion is selected.

For example, if an angle Z is 10 degrees from the longitudinal axis, when motion of the tube mount assembly 132 toward and away from the wallstand is selected, the motion of the tube mount assembly 132 along the longitudinal positioning rails (122 in FIG. 1) is D cosine(10) which is 0.9848D where D is a distance of the motion. Hence, the motion along the lateral positioning rails (124 in FIG. 1) is D sine(10) which is 0.1736D. In this example, the motion along the longitudinal positioning rails 0.9848D is greater than the motion of the tube mount assembly 132 along the lateral positioning rails, therefore, the longitudinal axis would be released for motion.

In some embodiments of selecting 502, the axis of the tube mount assembly 132 that has a larger linear movement for motion in the direction of motion is selected in reference to a look-up table or an equation in Table 1 as follows:

TABLE 1

$$Y = X \tan(Z) + K$$

In Table 1, Y is the position of the other axis, relative to a starting or reference point, X is the position of the axis being moved manually, relative to the starting or reference point, Z is the angle of the selected image receptor (106 or 108 in FIG. 1) relative to the lateral positioning rails 124 and longitudinal positioning rails 122, and K is a constant. It should be noted that in some embodiments, the angle Z is the angle of rotation of the tube mount assembly (132 in FIG. 1) about the vertical axis 116 of the overhead tube support (OTS) 110.

Thereafter, method 500 includes releasing 504 the selected axis of the tube mount assembly 132. In some embodiments, releasing the axis includes opening a clutch and releasing a brake.

Subsequently, method 500 includes manually moving 506 the equipment along the released axis. If the operator pushes along an axis that is not released, the equipment will not move significantly.

FIG. 6 is a flowchart of a method 600 of positioning radiographic equipment performed by a processor, such as processor 1104 in FIG. 11 according to an embodiment. Method 600 includes measuring 602 the position and/or relative motion of the axis which has been released for motion of the tube mount assembly 132, on an intermittent or continuous basis, as the tube mount assembly 132 is being moved manually, by means of a potentiometer, encoder, or the like. One embodiment of measuring 602 is described in FIG. 7 below and another embodiment of measuring 602 is described below in FIG. 8.

Thereafter, method 600 includes determining 604 a position for another axis of the tube mount assembly 132. In one embodiment, the position is determined in reference to a look up table. In another embodiment, the position is determined in reference to the equation in Table 1 above. One embodiment of determining 604 is described in FIG. 9 below.

Subsequently, the other axis is moved 606 or driven to the position determined in action 604. In some embodiments, a motorized drive of the other axis is employed by a control unit 144 to move the axis.

Method 600 positions the tube mount assembly 132 relative to each image receptor in the horizontal plane.

Methods 500 and 600 provide a method of manual positioning, in which some automatic motions and other improved features are incorporated in order to increase the utility of the equipment. Methods 500 and 600 provide a means to easily move the tube mount assembly, in a manner which is intuitive to the operator of the equipment, and which facilitates positioning and aligning the equipment properly in the room.

Figure 7:
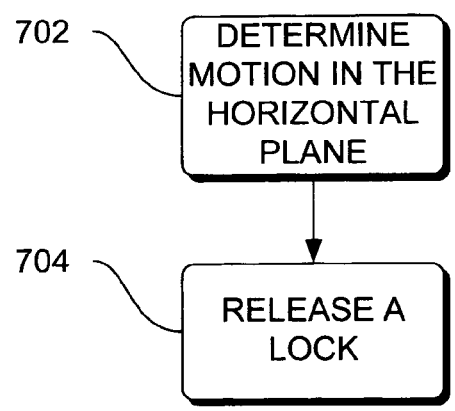
FIG. 7 is a flowchart of a method to measure the position and/or relative motion of an axis which has been released, according to an embodiment.

FIG. 7 is a flowchart of a method 700 to measure the position and/or relative motion of an axis which has been released, according to an embodiment. Method 700 is one embodiment of the measuring action 602 in FIG. 6 above. Method 700 provides simple and intuitive manual motion of the tube mount assembly (132 in FIG. 1).

Method 700 includes determining 702 directions of motion in the horizontal plane from the angle of rotation of the tube/collimator assembly about the vertical axis (118 in FIG. 1) of the tube mount assembly 132. When in the rotational detent position for a particular receptor (106 or 108), the resulting motions will be relative to the receptor, because the angle of the tube mount assembly 132 and the receptor 106 or 108 will be about equal. One effect is that manual motion of the tube mount assembly 132 will always be in the same relative direction to the tube mount assembly 132.

Thereafter, method 700 includes releasing 704 one lock. The released lock will allow a motion transverse to the user interface. Releasing another lock will result in motion in and out of the user interface. This provides for simplified motion of the tube mount assembly 132 for all manual positioning. From the perspective of the operator, the buttons correspond to lock releases and the directions of across the user interface and in and out of the user interface.

Figure 8:
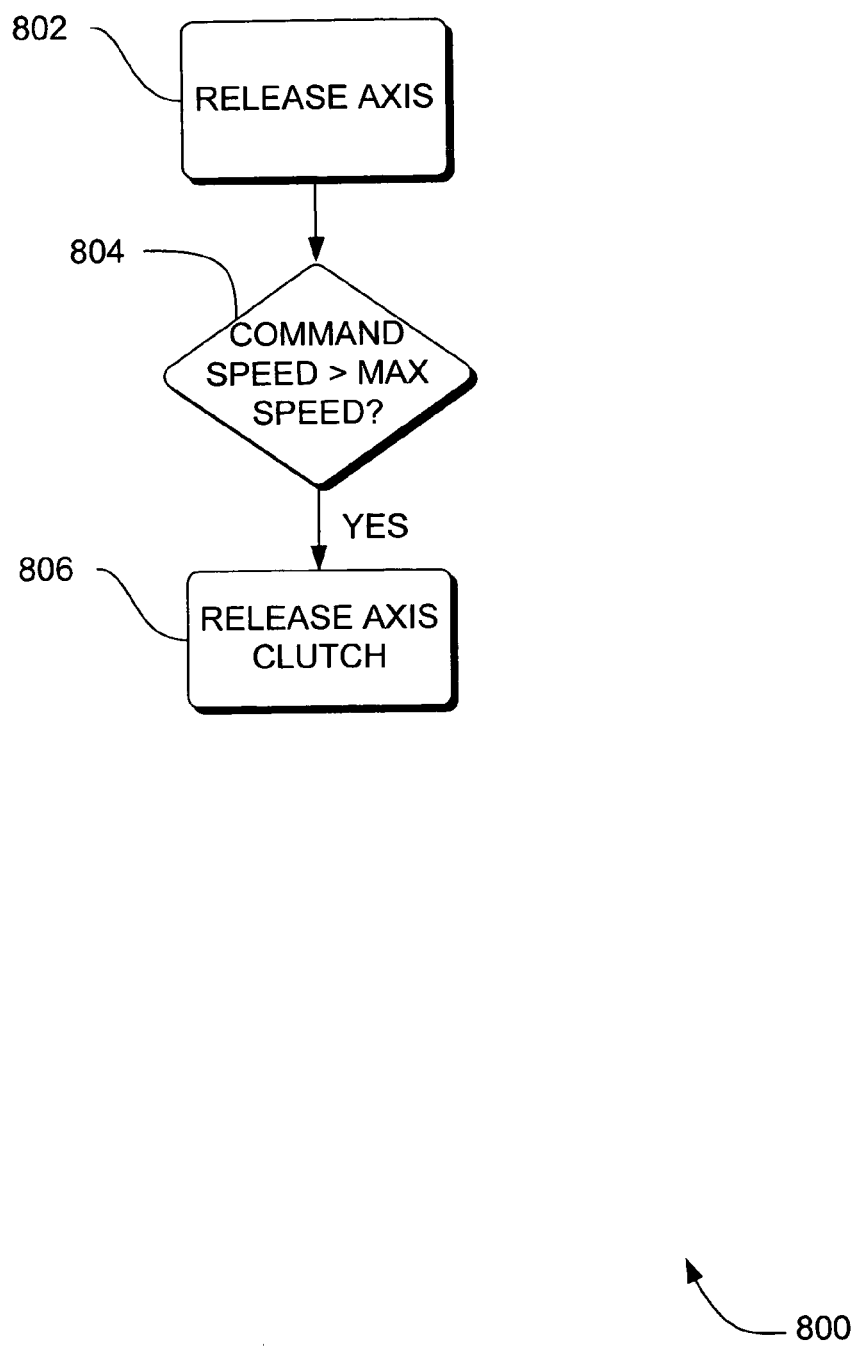
FIG. 8 is a flowchart of a method to measure the position and/or relative motion of an axis which has been released, according to an embodiment.

FIG. 8 is a flowchart of a method 800 to measure the position and/or relative motion of an axis which has been released, according to an embodiment. Method 800 is one embodiment of the measuring action 602 in FIG. 6 above. Method 800 provides simple and intuitive manual motion of the tube mount assembly (132 in FIG. 1) when the tube mount assembly 132 is not in a detent position and wherein the motion directions are determined by the selection of the receptor. Method 800 solves the need in the art to manually move the tube mount assembly 132 significantly faster than it would reasonably be driven.

Method 800 includes releasing 802 a lock on a first axis of movement of the equipment, to permit manual motion along that first axis. The system commands the speed along that axis in reference to the angle and the speed along another axis that is manually driven. Method 800 also includes determining 804 if a speed of movement of the equipment is commanded by the system along a second axis of movement if the equipment is greater than a maximum speed. If so then, a clutch is released 806. The clutch connects a motorized drive to a positioning rail in the second axis. Releasing 806 the clutch allows the equipment to move freely along the first axis and the second axis. In some embodiments, the released clutch allows both horizontal axes to move freely.

Methods 200, 300, 400, 600, 700 and 800 can be embodied as computer hardware circuitry or as a computer-readable program, or a combination of both.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in processor 1104 in FIG. 11, or on at least as many computers as there are components.

Apparatus of an Embodiment

In the previous section, a system level overview of the operation of an embodiment was described. In this section, the particular apparatus of such an embodiment are described by reference to a series of diagrams.

Figure 9:
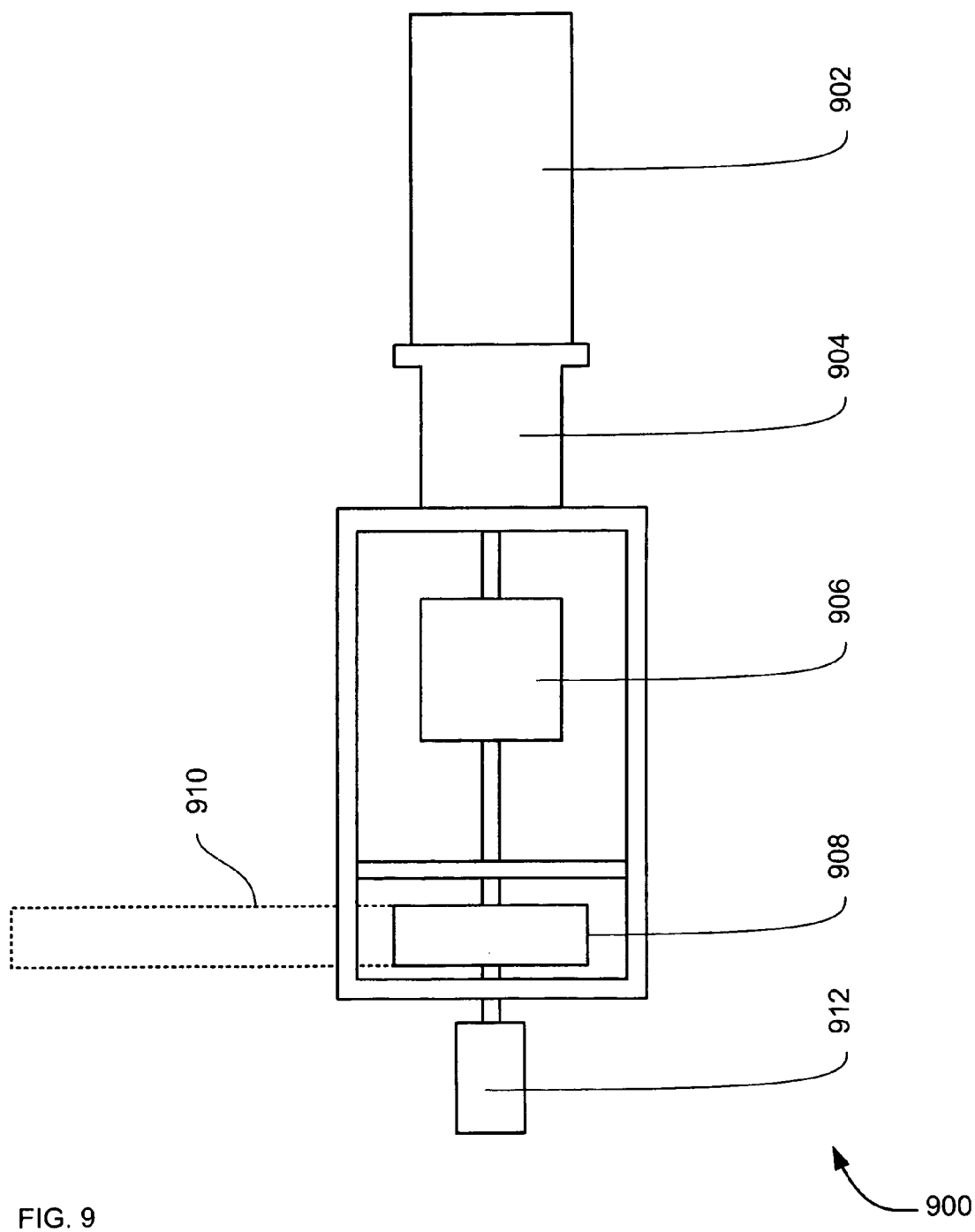
FIG. 9 is a top-view of a motorized drive apparatus according to an embodiment.

FIG. 9 is a top-view of a motorized drive apparatus 900 according to an embodiment. Motorized drive apparatus 900 implements the method of determining a position for another axis of the tube mount assembly, action 604 in FIG. 6 above.

Motorized drive apparatus 900 includes driving means 902, such as direct current (DC) motor. In some embodiments, motorized drive apparatus 900 further includes a speed reduction means 904, such as a gear reducer. In some embodiments motorized drive apparatus 900 further includes a clutch 906 or similar means to engage and disengage the driving means, allowing manual motion of the equipment when disengaged, and permitting powered driving of the equipment by the driving means when engaged. Motorized drive apparatus 900 additionally includes a wheel 908 engaged to a belt 910, cable, or toothed wheel connecting the driving means to a stationary member, allowing the driving means 902 to drive the equipment such as a tube mount assembly 132 relative to the stationary member. Motorized drive apparatus 900 also includes a position measuring means 912, such as an encoder, potentiometer or a resolver.

In some embodiments, the motorized drive apparatus 900 is coupled to the controller 906 in FIG. 9 or control unit 144 in FIG. 1 to provide computer control for the motorized drive apparatus 900.

In some embodiments, a brake or lock is attached to a belt, a cable, or a toothed wheel 910, to provide additional resistance to manual motion when in the target or dentent position.

Figure 10:
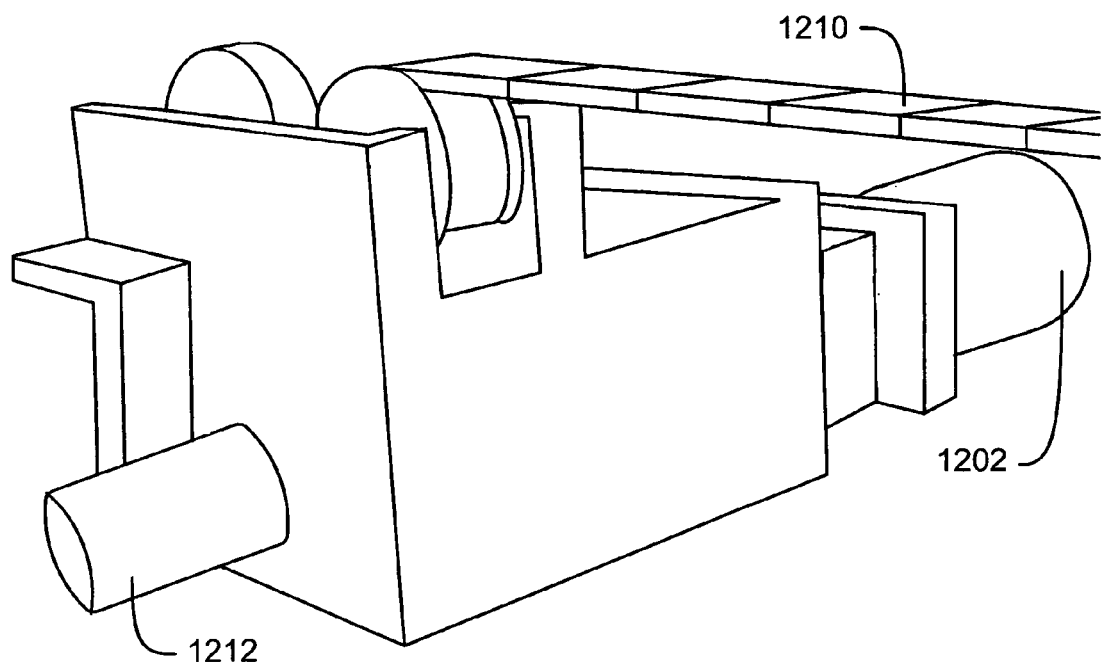
FIG. 10 is a perspective side-view of a motorized drive apparatus according to an embodiment.

FIG. 10 is a perspective side-view of a motorized drive apparatus 900 according to an embodiment. Apparatus 900 includes a driving means 902, a belt 910 and a position measuring means 912, such as an encoder, potentiometer or a resolver.

Hardware and Operating Environment

FIG. 11 is a block diagram of the hardware and operating environment 1100 in which different embodiments can be practiced. The description of FIG. 11 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also can be implemented in client/server computing environments where remote devices that perform tasks are linked through a communications network. Program modules can be located in both local and remote memory storage devices in a distributed computing environment.

Computer 1102 includes a processor 1104, commercially available from Intel, Motorola, Cyrix and others. Computer 1102 also includes random-access memory (RAM) 1106, read-only memory (ROM) 1108, and one or more mass storage devices 1110, and a system bus 1112, that operatively couples various system components to the processing unit 1104. The memory 1106, 1108, and mass storage devices, 1110, are types of computer-accessible media. Mass storage devices 1110 are more specifically types of nonvolatile computer-accessible media and can include one or more hard disk drives, floppy disk drives, optical disk drives, and tape cartridge drives. The processor 1104 executes computer programs stored on the computer-accessible media.

Computer 1102 can be communicatively connected to the Internet 1114 via a communication device 1116. Internet 1114 connectivity is well known within the art. In one embodiment, a communication device 1116 is a modem that responds to communication drivers to connect to the Internet via what is known in the art as a "dial-up connection." In another embodiment, a communication device 1116 is an Ethernet® or similar hardware network card connected to a local-area network (LAN) that itself is connected to the Internet via what is known in the art as a "direct connection" (e.g., T1 line, etc.).

A user enters commands and information into the computer 1102 through input devices such as a keyboard 1118 or a pointing device 1120. The keyboard 1118 permits entry of textual information into computer 1102, as known within the art, and embodiments are not limited to any particular type of keyboard. Pointing device 1120 permits the control of the screen pointer provided by a graphical user interface (GUI) of operating systems such as versions of Microsoft Windows®. Embodiments are not limited to any particular pointing device 1120. Such pointing devices include mice, touch pads, trackballs, remote controls and point sticks. Other input devices (not shown) can include a microphone, joystick, game pad, satellite dish, scanner, or the like.

In some embodiments, computer 1102 is operatively coupled to a display device 1122. Display device 1122 is connected to the system bus 1112. Display device 1122 permits the display of information, including computer, video and other information, for viewing by a user of the computer. Embodiments are not limited to any particular display device 1122. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1124 and 1126 provide audio output of signals. Speakers 1124 and 1126 are also connected to the system bus 1112.

Computer 1102 also includes an operating system (not shown) that is stored on the computer-accessible media RAM 1106, ROM 1108, and mass storage device 1110, and is and executed by the processor 1104. Examples of operating systems include Microsoft Windows®, Apple MacOS®, Linux®, UNIX®. Examples are not limited to any particular operating system, however, and the construction and use of such operating systems are well known within the art.

Embodiments of computer 1102 are not limited to any type of computer 1102. In varying embodiments, computer 1102 comprises a PC-compatible computer, a MacOS®-compatible computer, a Linux®-compatible computer, or a UNIX®-compatible computer. The construction and operation of such computers are well known within the art.

Computer 1102 can be operated using at least one operating system to provide a graphical user interface (GUI) including a user-controllable pointer. Computer 1102 can have at least one web browser application program executing within at least one operating system, to permit users of computer 1102 to access intranet or Internet world-wide-web pages as addressed by Universal Resource Locator (URL) addresses. Examples of browser application programs include Netscape Navigator® and Microsoft Internet Explorer®.

The computer 1102 can operate in a networked environment using logical connections to one or more remote computers, such as remote computer 1128. These logical connections are achieved by a communication device coupled to, or a part of, the computer 1102. Embodiments are not limited to a particular type of communications device. The remote computer 1128 can be another computer, a server, a router, a network PC, a client, a peer device or other common network node. The logical connections depicted in FIG. 11 include a local-area network (LAN) 1130 and a wide-area network (WAN) 1132. Such networking environments are commonplace in offices, enterprise-wide computer networks, intranets and the Internet.

When used in a LAN-networking environment, the computer 1102 and remote computer 1128 are connected to the local network 1130 through network interfaces or adapters 1134, which is one type of communications device 1116. Remote computer 1128 also includes a network device 1136. When used in a conventional WAN-networking environment, the computer 1102 and remote computer 1128 communicate with a WAN 1132 through modems (not shown). The modem, which can be internal or external, is connected to the system bus 1112. In a networked environment, program modules depicted relative to the computer 1102, or portions thereof, can be stored in the remote computer 1128.

Computer 1102 also includes power supply 1138. Each power supply can be a battery.

CONCLUSION

A radiographic positioner has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in terms or radiographic equipment, one of ordinary skill in the art will appreciate that implementations can be made or any other industrial application that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future radiographic devices and new industrial control apparatus. The invention herein described can be implemented on any electromechanical system which allows both manual and driven motion, and provides feedback of position.

The terminology used in this application with respect to control unit is meant to include process and computing environments and alternate technologies which provide the same functionality as described herein.

We claim:

1. A system having executable instructions to allow manual motion of X-ray tube and collimator, in which the X-ray tube and collimator are mounted on an extending column, and in which the X-ray tube and collimator are controlled by a processor through a motorized drive, the system comprising:
   a means for releasing a lock on a first horizontal axis of movement of the X-ray tube and collimator;
   a means for determining if a speed of movement of the X-ray tube and collimator that is commanded by the processor along a second horizontal axis of movement of the X-ray tube and collimator are greater than a maximum speed; and
   a means for releasing a clutch that connects the motorized drive to a positioning rail in the second horizontal axis, which allows the X-ray tube and collimator to move freely along the first horizontal axis and the second horizontal axis.

2. The system of claim 1, wherein the first horizontal axis further comprises a horizontal lateral axis and the second horizontal axis further comprises a horizontal longitudinal axis.

3. The system of claim 1, wherein the first horizontal axis further comprises a horizontal longitudinal axis and the second horizontal axis further comprises a horizontal lateral axis.

4. The system of claim 1 further comprising:
   a plurality of longitudinal positioning rails mounted on a ceiling, the being ceiling above the system;
   a plurality of lateral positioning rails operably coupled to the plurality of longitudinal positioning rails;
   a carriage operably coupled to the plurality of lateral positioning rails;
   an overhead tube support operably coupled to the carriage;
   an image receptor; and
   at least one positioning rail being positioned at an angle other than zero degrees and ninety degrees about a vertical axis relative to the image receptor.

5. The system of claim 4, wherein the angle other than zero degrees and ninety degrees comprises an angle which differs from zero degrees and ninety degrees by at least 5 degrees.

6. The system of claim 4, wherein the angle other than zero degrees and ninety degrees comprises an angle which differs from zero degrees and ninety degrees by at least 10 degrees.

7. The system of claim 1, further comprising an image receptor positioned below the positioning rail and wherein the positioning rail further comprises being operable to be positioned at an angle other than zero degrees and ninety degrees relative to the image receptor; and the X-ray tube and collimator further comprise being operable to move along and across relative to the image receptor.

8. The system of claim 7, wherein the angle other than zero degrees and ninety degrees comprises an angle which differs from zero degrees and ninety degrees by at least 5 degrees.

9. The system of claim 7, wherein the positioning rail further comprises:
   a first plurality of horizontal positioning rails; and
   a second plurality other two horizontal positioning rails operably coupled to the two horizontal positioning rails.

10. The system of claim 7, further comprising:
    an imaging wallstand operably coupled to the image receptor.

11. The system of claim 7, further comprising:
    an imaging table operably coupled to the image receptor.

12. The system of claim 7, wherein, the image receptor further comprises:
    a digital image receptor.

13. The system of claim 7, wherein, the X-ray tube further comprises:
    a medical X-ray source.

14. The system of claim 7, further comprising:
    a medical digital image receptor positioned below the positioning rail;
    a first plurality of horizontal positioning rails being positioned at an angle other than zero degrees and ninety degrees relative to the digital image receptor; and
    a second plurality of horizontal positioning rails moveably coupled to the two the horizontal positioning rails and positioned at an angle other than zero degrees and ninety degrees relative to the digital image receptor.

15. The system of claim 14, further comprising:
    an imaging wallstand operably coupled to the image receptor.

16. The system of claim 14, further comprising:
    an imaging table operably coupled to the image receptor.

17. The system of claim 1, further comprising:
    a second motorized drive to provide motion along a lateral axis, a third motorized drive to provide motion along a vertical axis,
a fourth motorized drive to provide motion along a rotational vertical axis, and
a fifth motorized drive to provide motion along a rotational horizontal axis; and
wherein the processor is operably coupled to each of the motorized drives.

18. The system of claim 17, wherein the processor further comprises: control logic operable to:
select a rotational detent to the extent that at least one of the axes is aligned to a radiographic image receptor; and
constrain movement of the at least one axis to the extent that manual positioning is along and across a plane parallel to the radiographic image receptor.

19. The system of claim 17, further comprising:
a plurality of longitudinal positioning rails mounted on a ceiling;
a plurality of lateral positioning rails operably coupled to the plurality of longitudinal positioning rails through the first motorized drive;
a carriage operably coupled to the plurality of lateral positioning rails through the second motorized drive; and
an overhead tube support operably coupled to the carriage through at the third motorized drive.

20. The system of claim 19, wherein the overhead tube support further comprises:
an extending column that includes a plurality of stacked slides that are mounted to each other through linear bearing assemblies that allow the extending column to telescope inward and outward.

21. The system of claim 1, further comprising:
a plurality of longitudinal positioning rails mounted on a ceiling;
a plurality of lateral positioning rails operably coupled to the plurality of longitudinal positioning rails through at the first motorized drive;
a carriage operably coupled to the plurality of lateral positioning rails through a second motorized drive;
an overhead tube support operably coupled to the carriage through a third motorized drive a fourth motorized drive;
the X-ray tube being operably coupled to the overhead tube support through a fifth motorized drive; and
the processor being operably coupled to the first motorized drive, the second motorized drive, the third motorized drive, the fourth motorized drive and the fifth motorized drive.

22. The system of claim 21, further comprising:
a storage device coupled to the processor; and
control logic operable on the processor to:
select a rotational detent to the extent that the X-ray tube and collimator are aligned to a radiographic image receptor; and
constrain movement of the X-ray tube and collimator to the extent that manual positioning is along and across a plane parallel to the image receptor.

23. The system of claim 21, wherein the overhead tube support further comprises:
an extending column that further includes a plurality of stacked slides that are mounted to each other through linear bearing assemblies that allow the extending column to telescope inward and outward.

24. The system of claim 1, wherein an overhead tube support is manually positioned so that proper alignment is maintained to a radiographic image receptor without regard to an angle about a vertical rotation axis at which the radiographic image receptor and the overhead tube support are positioned relative to each other, wherein the manual positioning comprises:
selecting a rotational detent to the extent that the overhead tube support is aligned to the radiographic image receptor; and
constraining movement of the tube mount assembly to the extent that manual positioning is along and across a plane parallel to the image receptor.

25. The system of claim 24, wherein the selecting further comprises:
determining at least one detent position for the vertical rotation axis of the overhead tube support from an angle at which the radiographic image receptor is positioned relative to a lateral positioning rail and a longitudinal positioning rail.

26. The system of claim 25, wherein the radiographic image receptor further comprises:
a radiographic image receptor mounted to a radiographic table.

27. The system of claim 26, wherein the radiographic image receptor further comprises:
a radiographic image receptor mounted to a radiographic wallstand.

28. The system of claim 24, wherein the constraining further comprises:
constraining movement of the tube mount assembly to the extent that manual positioning is not along a lateral positioning rail and a longitudinal positioning rail.

29. A computer-accessible medium having executable instructions to allow manual motion of equipment, in which the equipment is mounted on an extending column, and in which the equipment is controlled by a processor through a motorized drive, the executable instructions configured to direct the processor to perform:
releasing a lock on a first axis of movement of the equipment, to permit manual motion along the first axis;
determining if a speed of movement of the equipment that is commanded by the processor along a second axis of movement of the equipment is greater than a maximum speed; and
releasing a clutch that connects the motorized drive to positioning rail in the second axis, which allows the equipment to move freely along the first axis and the second axis.

30. The computer-accessible medium of claim 29, wherein the equipment further comprises an X-ray tube and a collimator.

31. The computer-accessible medium of claim 29, wherein the first axis further comprises a horizontal axis and the second axis further comprises the other horizontal axis.

32. A computer-accessible medium having executable instructions to allow manual motion of X-ray tube and collimator, in which the X-ray tube and collimator are mounted on an extending column, and in which the X-ray tube and collimator are controlled by a processor through a motorized drive, the executable instructions configured to direct the processor to perform:
releasing a lock on a first horizontal axis of movement of the medical imaging equipment, to permit manually powered movement along the first horizontal axis of movement;
determining if a speed of movement of the X-ray tube and collimator that is commanded by the processor along a second horizontal axis of movement of the X-ray tube and collimator are greater than a maximum speed; and releasing a clutch that connects the motorized drive to positioning rail in the second horizontal axis, which allows the X-ray tube and collimator to move freely along the first horizontal axis and the second horizontal axis.

33. The computer-accessible medium of claim 32, wherein the first horizontal axis further comprises a horizontal lateral axis and the second horizontal axis further comprises a horizontal longitudinal axis.

34. The computer-accessible medium of claim 32, wherein the first horizontal axis further comprises a horizontal longitudinal axis and the second horizontal axis further comprises a horizontal lateral axis.

35. A method to allow manual motion of a medical imaging equipment, in which the medical imaging equipment is mounted on an extending column, and in which the medical imaging equipment is controlled by a processor through a motorized drive, the method comprising:

releasing a lock on a first horizontal axis of movement of the medical imaging equipment, to permit manually powered movement along the first horizontal axis of movement;

determining if a speed of movement of the medical imaging equipment that is commanded by the processor along a second horizontal axis of movement of the medical imaging equipment are greater than a maximum speed and;

releasing a clutch that connects the motorized drive to positioning rail in the second horizontal axis, which allows the medical imaging equipment to move freely along the first horizontal axis and the second horizontal axis.

36. The method of claim 35, wherein the first horizontal axis further comprises a horizontal lateral axis and the second horizontal axis further comprises a horizontal longitudinal axis.

37. The method of claim 35, wherein the first horizontal axis further comprises a horizontal longitudinal axis and the second horizontal axis further comprises a horizontal lateral axis.

38. A computer-accessible medium to allow manual motion of an X-ray tube and collimator, in which the X-ray tube and collimator are mounted on an extending column, and in which the X-ray tube and collimator are controlled by a processor through a motorized drive, the computer-accessible medium comprising:

a releaser of a lock on a first horizontal axis of movement of the X-ray tube and collimator;

a determiner of a speed of movement of the X-ray tube and collimator that is commanded by the processor along a second horizontal axis of movement of the X-ray tube and collimator are greater than a maximum speed; and a releaser of a clutch that connects the motorized drive to positioning rail in the second horizontal axis, which allows the X-ray tube and collimator to move freely along the first horizontal axis and the second horizontal axis.

39. The computer-accessible medium of claim 38, wherein the first horizontal axis further comprises a horizontal lateral axis and the second horizontal axis further comprises a horizontal longitudinal axis.

* * * * *